United States Patent
Renger

[11] Patent Number: 5,961,540
[45] Date of Patent: Oct. 5, 1999

[54] PANCAKE ANNUNCIATOR

[75] Inventor: Herman Lee Renger, Calabasas, Calif.

[73] Assignee: Pacesetter, Inc., Sylmar, Calif.

[21] Appl. No.: 08/906,672

[22] Filed: Sep. 5, 1997

[51] Int. Cl.[6] .......................... A61B 5/103; A61N 1/375
[52] U.S. Cl. ................... 607/32; 607/60; 607/19; 600/595; 335/222; 340/392.1; 73/488; 73/570
[58] Field of Search .................. 607/32, 27, 29, 607/36, 60, 19; 340/286.11, 407.1, 467, 480, 815.79, 384.7, 392.1, 669, 670, 690; 73/488, 570, 865.4; 335/222, 229; 600/587, 595

[56] References Cited

U.S. PATENT DOCUMENTS

| | | |
|---|---|---|
| 3,783,877 | 1/1974 | Bowers . |
| 3,841,305 | 10/1974 | Hallgren . |
| 4,086,916 | 5/1978 | Freeman et al. . |
| 4,088,139 | 5/1978 | Auerbach . |
| 4,102,346 | 7/1978 | Fulker . |
| 4,210,149 | 7/1980 | Heilman et al. . |
| 4,295,474 | 10/1981 | Fischell . |
| 4,345,603 | 8/1982 | Schulman . |
| 4,407,289 | 10/1983 | Nappholz et al. . |
| 4,892,100 | 1/1990 | Schaldach . |
| 5,107,540 | 4/1992 | Mooney et al. ............... 381/192 |
| 5,172,092 | 12/1992 | Nguyen et al. ............... 340/311.1 |
| 5,190,034 | 3/1993 | Sholder . |
| 5,623,248 | 4/1997 | Min ............................. 340/540 |
| 5,682,132 | 10/1997 | Hiroyoshi .................... 340/407.1 |
| 5,709,225 | 1/1998 | Budgifvars et al. .......... 128/899 |
| 5,745,019 | 4/1998 | Renger ........................ 335/222 |

Primary Examiner—Jeffrey R. Jastrzab

[57] ABSTRACT

An annunciator for an implantable medical device encapsulated within a casing comprises a magnetically permeable stationary ring member including an integral inwardly projecting peripheral flange having opposed sides on which electrically conductive coils are mounted. An oscillating member encompassed by the stationary ring member includes a planar magnet member having opposed surfaces of opposite polarity and planar pole pieces are mounted to the first and second surfaces, respectively, in a sandwich-like construction. The oscillating member is movable along a longitudinal axis between extreme positions whereat the first pole piece, then the second pole piece is proximate the ring flange. Cyclic energization of the electrically conductive coils generates a cyclically alternating magnetic field, which interacts with the magnetic field of the oscillating member causing its oscillation between the first and second extreme positions. In another embodiment, the casing includes opposed walls and the first and second pole pieces impact against the opposed walls when the oscillating member reaches the first and second extreme positions, respectively. In another embodiment, opposed spider members have a central portion fixed to their respective polar pieces and a plurality of radially extending legs have terminal ends fixed, respectively, to the ring member at peripherally spaced locations, the spider members being axially compliant and biasing the oscillating member toward a neutral position and being substantially non-compliant transversely of the longitudinal axis for centering the oscillating member relative to the ring member throughout travel thereof between the first and second extreme positions.

15 Claims, 3 Drawing Sheets

PANCAKE ANNUNCIATOR

FIELD OF THE INVENTION

The present invention relates to annunciator devices for medical devices implantable in the body of a patient and in particular to such devices which may be used in combination with implantable defibrillator systems, for example, and be assured of attracting the attention of the patient upon the occurrence of a predetermined event.

BACKGROUND OF THE INVENTION

Implantable defibrillation systems, as one instance of implantable medical devices, are known in the art which deliver a high-voltage defibrillation pulse to the heart when the onset of fibrillation is detected and/or in the event of a detected complete loss of cardiac output. Such known devices are also capable, if the heart exhibits an arrhythmia such as atrial fibrillation, atrial flutter or tachycardia, or ventricular tachycardia, of cardioverting the heart by delivering a low-voltage pulse in an attempt to regain synchronous operation of the heart, instead of delivering the high voltage defibrillation pulse. In known devices of this type, considerable effort has been devoted to the development of detection circuitry to accurately identify heart arrhythmias which require defibrillation or cardioversion (i.e., insuring true-positives) and for preventing a "no output" situation when an output is actually needed (i.e., preventing true-negatives). Steps have also been taken to prevent the delivery of a defibrillation or cardioversion pulse when none is needed (i.e., preventing false-positives). See, for example, commonly assigned U.S. Pat. No. 5,190,034, to Sholder.

It is important to provide a safety mechanism for preventing implantable systems of this type from releasing a treatment pulse when-the patient feels no need for such a pulse. A false-positive output could result in severe discomfort to the patient, and may trigger ventricular tachycardia, ventricular fibrillation and ultimately death if the system cannot react quickly enough to provide proper treatment to revive the patient.

In U.S. Pat. No. 3,841,305, to Hallgren, a system is disclosed for the external stimulation of a nerve and includes a coil of wire with a flux-concentrating core in the lumen of the coil. The core preferably has a T-shape with the base of the T extending through the lumen of the coil providing the area of stimulation. The coil is pulsed by a discharging capacitor and circuitry is disclosed for charging the capacitor and generating discharge pulses of alternate polarity.

It is known from U.S. Pat. No. 4,086,916, to Freeman et al., to contain a cardiac monitoring system in a wristwatch worn by a patient, the system including circuitry for detecting an erratic heartbeat, a missing pulse or other irregularities and providing an alarm indication, audio and visual, when such an event is detected.

It is also known from U.S. Pat. No. 4,088,139, to Auerbach, to provide, in an implantable cardiac pacing system, means for generating a marking pulse in the defibrillator monitoring system if an event such as loss of capture occurs. The patient is not immediately informed of the occurrence of such an event, however, the system is provided with telemetry means so that when the recorded data is subsequently read out and examined by a physician, the data will include the marker indicating that loss of capture has occurred. The physician can then take such corrective steps as may be necessary.

An implantable pacing system is disclosed in U.S. Pat. No. 4,102,346, to Fulker, which includes an alarm device as part of the implanted unit which generates an alarm signal to inform the defibrillator user when the battery source of power of the defibrillator is nearing end-of-life or is malfunctioning.

An implantable tissue stimulating device is disclosed in U.S. Pat. No. 4,345,603, to Schulman, which activates an alarm which informs the patient in whom the system is implanted that the battery is in need of replacement. After the user has been so informed, the user applies a magnet externally in the vicinity of the implanted unit to deactivate the monitoring system and thereby cease the continued operation of the alarm.

A pacemaker for controlling tachycardia is disclosed in U.S. Pat. No. 4,407,289, to Nappholz et al., also disclosing means for informing a pacemaker user of the remaining battery life. The user places a magnet externally in the vicinity of the implanted unit, which thereby causes the implanted unit to generate two pulses, which can be seen on the patient's ECG waveform. The time separation between the two pulses indicates the remaining battery potential. Application of the magnet, after the pulses have been generated, temporarily disables the device.

U.S. Pat. No. 4,892,100, to Schaldach, discloses a demand pacemaker with physiological control intended to simplify adaptation to the individual patient and thus make it possible that, in addition to initial adaptation to the individual stimulation requirements, the operating behavior of the pacemaker can continuously be brought up to date to correspond to changing demands for stimulation.

In U.S. Pat. No. 5,190,034, noted earlier, an implantable arrhythmia treatment system is disclosed which includes reliable protection against the release of unneeded treatment pulses, that is, which provides protection against a false-positive output. The disclosed system utilizes an alarm generator, which may be disposed in the implanted unit, or in an external unit. The alarm may be of any type which does not require constant, active monitoring by the user, such as a sensory alarm, for example, an audio alarm generator or a tactile alarm generator or "tickler".

Other examples of implantable arrhythmia devices which include an alarm generator, either audio, tactile, or visual, are found in U.S. Pat. Nos. 4,295,474, to Fischell; 4,210,149, to Heilman et al.; and 3,783,877, to Bowers.

According to the current state of the art, error conditions are typically announced within an implantable cardioverter defibrillator (ICD) using a piezo annunciator or beeper. The current Eagle Model 2800 in development by Pacesetter, Inc., a St. Jude Medical Company, Sylmar, Calif., utilizes a piezo actuator to flex the titanium can at audio frequencies. However, the efficacy of audio emissions from devices implanted abdominally can be questioned. The attenuation of the audio transmitted through tissue is dramatic. Aged patients commonly have hearing loss that further decreases their sensitivity to implanted audio generators.

It was in light of the foregoing that the present invention was conceived and has now been reduced to practice.

SUMMARY OF THE INVENTION

According to the invention, an annunciator is provided for a medical device, which is implantable in the body of a patient. The annunciator is encapsulated within a casing for the medical device and comprises a magnetically permeable stationary ring member including an integral inwardly projecting peripheral flange having opposed sides on which electrically conductive coils are mounted. An oscillating member encompassed by the stationary ring member includes a planar magnet member having opposed surfaces of opposite polarity and planar pole pieces are mounted to the first and second surfaces, respectively, in a sandwich-like construction. The oscillating member is movable along a longitudinal axis between extreme positions whereat the first pole piece, then the second pole piece is proximate the peripheral flange. Cyclic energization of the electrically conductive coils generates a cyclically alternating magnetic field, which interacts with the magnetic field of the oscillating member causing its oscillation between the first and second extreme positions. In another embodiment, the casing includes opposed walls and the first and second pole pieces impact against the opposed walls when the oscillating member reaches the first and second extreme positions, respectively. In another embodiment, opposed spider members have a central portion fixed to their respective pole pieces and a plurality of radially extending legs have terminal ends fixed, respectively, to the ring member at peripherally spaced locations, the spider members being axially compliant and biasing the oscillating member toward a neutral position and being substantially non-compliant transversely of the longitudinal axis for centering the oscillating member relative to the ring member throughout travel thereof between the first and second extreme positions.

The annunciator of the invention operates magnetically and can be considered as being a cross between a solenoid and a voice coil. The moving section comprises a flat disk magnet, axially polarized and two flat disk pole pieces. A stationary section has two coils and an iron ring which has a "T" shaped cross section, the stem of the "T" pointing inward with its tip between the two moving pole faces. The magnetic field lines from the permanent magnet leave one pole face, pass through the tip of the stem of the "T" and then proceed to the other pole face. When the coils are driven with an electrical current, the tip of the "T" has a magnetic polarity and is attracted to one of the pole face disks while being repelled by the other. This produces an axial force, which is effective to move or accelerate a movable section of the annunciator. A spring or springs may be used to center the movable section and/or make it mechanically resonant at the driving frequency.

By interacting the fields from both the permanent magnet and the coils, the device of the invention is, in fact, self-generating accelerometer. If desired, the moving part can be made to impact a stop member to produce high frequency shock waves.

A primary object of the invention, therefore, is to provide an annunciator device which is implantable in the body of a patient, and, in particular, to such devices which may be used in combination with implantable defibrillator systems, for example, and be assured of attracting the attention of the patient upon the occurrence of a predetermined event.

A further object of the invention is to provide an annunciator for an implanted medical device such as a defibrillator, which produces vibration, and possibly sound, one, which utilizes low voltage and requires minimal space.

Another object of the invention is to provide a flat annunciator, which operates to efficiently vibrate an implanted package such as a defibrillator.

The device of the invention uses coils and a permanent magnet driven field structure to produce the forces and accelerations necessary to generate vibrations. In addition, it utilizes the sudden deceleration resulting when a relatively massive moving unit strikes a stop member to produce higher harmonics and sound. As implemented in one embodiment, this device uses multiple permanent magnets and multiple coil sections in order to obtain the greatest effect out of the space available.

Either pulsed DC or AC may be employed to drive the invention. A compression spring helps to position the magnetic structure with respect to the coils and makes the system mechanically resonant to improve efficiency.

An additional feature of the device described is that it can be used as an activity sensor. The moveable mass will be affected by acceleration or vibration of the patient and will generate a voltage on the terminals, which can easily be monitored.

The present invention offers numerous advantages. It provides a compact structure while using a relatively massive magnetic structure as a moving part. It also provides a novel annunciator device applicable to organ stimulating systems, which are implantable in a patient's body. More particularly, the invention may be used in combination with implantable defibrillator systems, for example, and be assured of attracting the attention of the patient upon the occurrence of a predetermined event. Alternatively, the invention may be operated to simultaneously produce an audible and a tactile vibration for use by a patient who may have experienced undue hearing loss.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENTS

Figure 1:
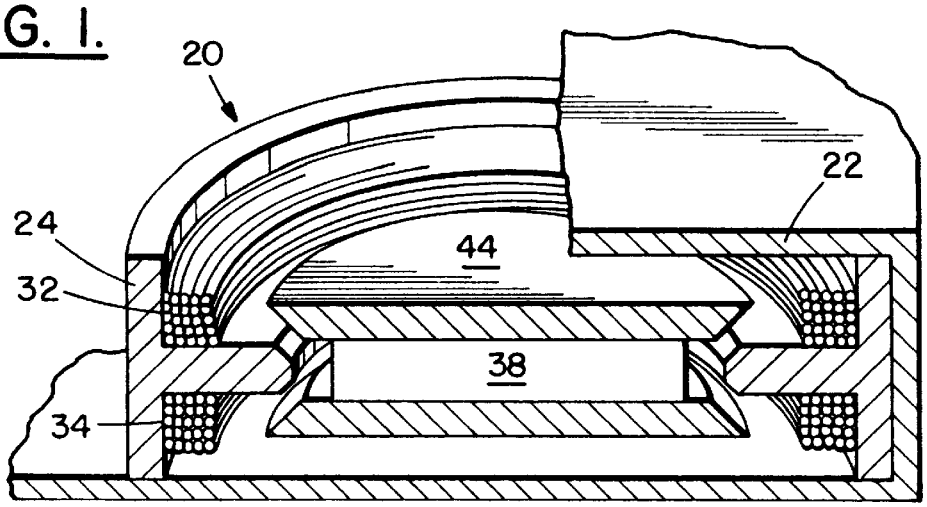
FIG. 1 is a diagrammatic perspective view of a medical device, such as a defibrillator, incorporating an annunciator embodying the present invention for an organ stimulating system implantable in the body of a patient.
Figure 2:
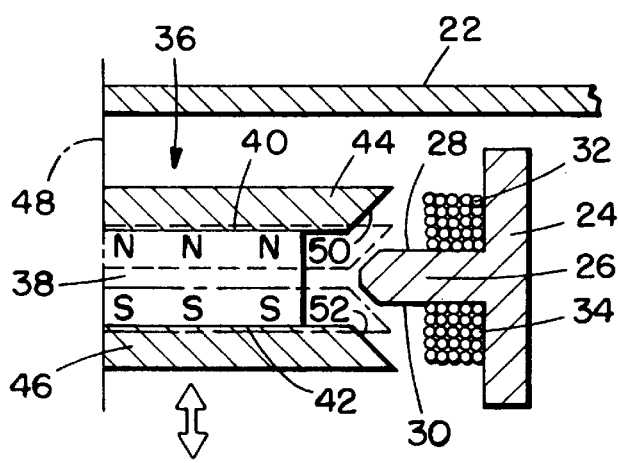
FIG. 2 is a diagrammatic detail side elevation view, in section, of the annunciator illustrated in FIG. 1.

Turn now to the drawings and, initially, to FIGS. 1 and 2 which diagrammatically illustrate an annunciator 20 embodying the present invention encapsulated within a casing 22 of a medical device such as a defibrillator and implantable in the body of a patient. The annunciator 20 comprises a magnetically permeable stationary ring member 24 including an integral inwardly projecting peripheral flange 26 having first and second opposed sides 28, 30, respectively. While the ring member 24 may be cylindrical, it may be of any suitable peripherally continuous shape. A first electrically conductive coil 32 is mounted on the peripheral flange 26 adjacent the first side 28 and a second electrically conductive coil 34 is mounted on the peripheral flange adjacent the second side 30.

An oscillating member 36 is encompassed by the stationary ring member 24 and includes a planar permanent magnet member 38 having first and second opposed surfaces 40, 42 of opposite polarity and first and second planar pole pieces 44, 46 suitably mounted to the first and second surfaces 40, 42, respectively, in a sandwich-like construction. The oscillating member has a longitudinal axis 48 and is movable along that axis between a first extreme position indicated by dashed lines in FIG. 2 at which the first pole piece 44 is proximate the peripheral flange 26 and a second extreme position indicated by intermittent dashed lines in FIG. 2 at which the second pole piece 46 is proximate the peripheral flange.

According to the invention, cyclic energization of the first and second electrically conductive coils 32, 34 with an electrical current generates a cyclically alternating magnetic field which interacts with the magnetic field of the oscillating member 36 to cause the oscillating member to oscillate between the first and second extreme positions as earlier defined and thereby produce the motion and/or sound which serves as an alarm or warning signal to the patient.

The first pole piece 44 includes an outermost region terminating at a first beveled surface 50 and, similarly, the second pole piece 46 includes an outermost region terminating at a second beveled surface 52. Cooperating with the oscillating member 36, the peripheral flange 26 includes an innermost region terminating at first and second beveled surfaces 54, 56, respectively. The beveled surface 50 of the first pole piece 44 impacts against and matingly engages the first beveled surface 54 of the peripheral flange 26 when the oscillating member 36 reaches the first extreme position and the beveled surface 52 of the second pole piece 46 impacts against and matingly engages the second beveled surface 56 of the peripheral flange when the oscillating member 36 reaches the second extreme position.

Figure 3:
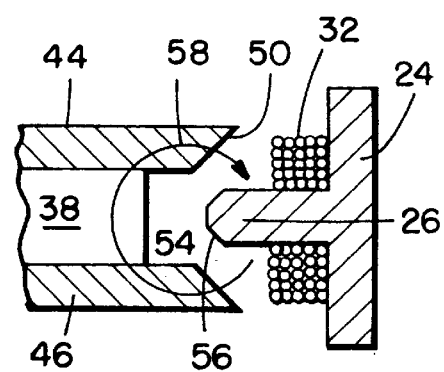
FIGS. 3, 4 and 5 are all diagrammatic side elevation views, in section, of parts illustrated in FIG. 2 for illustrating magnetic and magnetic field lines which result from operation of the invention.
Figure 5:
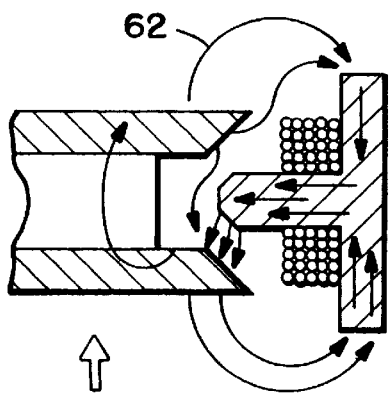
Figure 4:
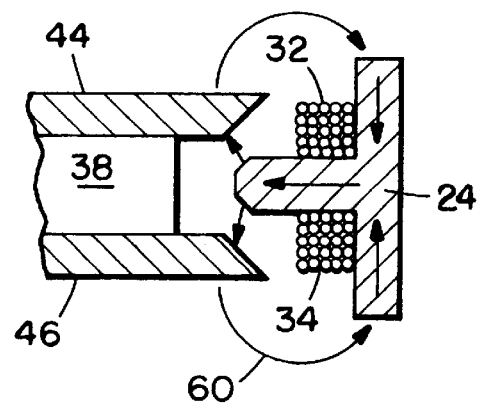

As seen in FIG. 3, magnetic field lines 58 from the permanent magnet member 38 leave one pole face, that is, surface 40, advance through the beveled surface 50, then through the beveled surface 54 into the peripheral flange 26. The magnetic field lines continue through an extremity of the peripheral flange 26 and then proceed, via beveled surfaces 56 and 52 to the other pole face, that is, surface 42. As seen in FIG. 4, when the conductive coils 32, 34 are driven with an electrical current, the extremity of the peripheral flange 26 is given a magnetic polarity as indicated by magnetic field lines 60 and attracted to one of the pole pieces 44, 46 while being repelled by the other. This produces an axial force to move or accelerate the oscillating member 36. FIG. 5 diagrammatically indicates modified field lines 62, which provide a depiction of the interaction between the magnetic field lines 58 (FIG. 3), and the magnetic field lines 60 (FIG. 4).

As will be described below, a spring or springs may be used to center the oscillating member and/or make it mechanically resonant at the driving frequency, biasing the oscillating member 36 toward a neutral position intermediate the first and second extreme positions.

Figure 6:
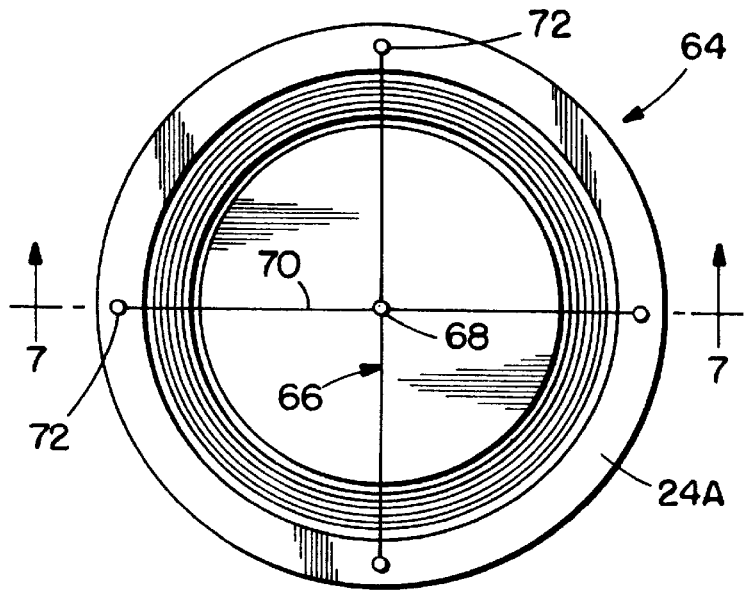
FIG. 6 is a plan view of a modified annunciator embodying the invention.
Figure 7:
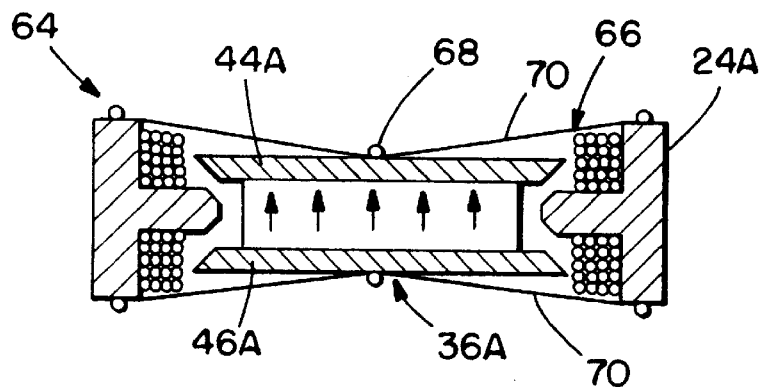
FIG. 7 is a diagrammatic cross section view taken generally along the line 7—7 in FIG. 6.

Accordingly, in a preferred construction viewing FIGS. 6 and 7, a modified annunciator 64 is illustrated. This modified annunciator includes a first spider member 66 having a central portion 68 fixed to a first pole piece 44A and a plurality of radially extending legs 70 with terminal ends 72 fixed, respectively, to the ring member 24A at peripherally spaced locations. The first spider member 66 is axially compliant and biases the oscillating member 36A toward a neutral (solid line, as illustrated) position intermediate the first and second extreme positions. At the same time, the first spider member 66 is substantially non-compliant transversely of the longitudinal axis for centering the oscillating member 36A relative to the ring member 24A throughout the course of its travel between the extreme positions. A second spider member 74, co-operable with the first spider member 66, is similarly configured and constructed but is attached to the second pole piece 46A rather than to the first pole piece 44A.

Figure 8:
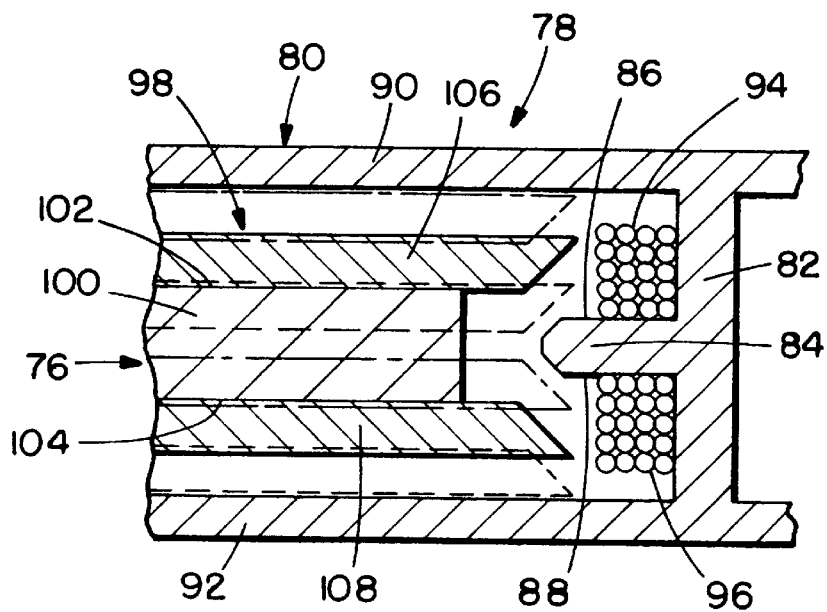
FIG. 8 is a diagrammatic cross section view, similar to FIG. 7 illustrating a modified construction of an annunciator embodying the invention together with a medical device, such as a defibrillator, and presenting another mode of operation thereof.

Another modified construction of the invention is illustrated in FIG. 8. In this instance, an annunciator 76 is shown in combination with a medical device 78, such as a defibrillator, encapsulated within a casing 80 and implantable in the body of a patient. A magnetically permeable stationary ring member 82 is fixed to the casing and includes an integral radially inwardly projecting peripheral flange 84 having opposed sides 86, 88 and positioned intermediate opposed sidewalls 90, 92 of the casing 80. A first electrically conductive coil 94 is mounted on the peripheral flange 84 adjacent the first side 86 and a second electrically conductive coil 96 is mounted on the peripheral flange adjacent the second side 88.

As with the earlier described embodiments, an oscillating member 98 is encompassed by the stationary ring member 92 and includes a planar permanent magnet member 100 having first and second opposed surfaces 102, 104 of opposite polarity and first and second planar pole pieces 106, 108 mounted to the first and second surfaces 102, 104, respectively, in a sandwich-like construction. The oscillating member is movable along its longitudinal axis from a neutral, solid line, position to a first extreme position indicated by dashed lines at which the first pole piece is proximate the peripheral flange 84 and a second extreme position indicated by intermittent dashed lines in FIG. 8 at which the second pole piece is proximate the peripheral flange.

In the manner previously explained with respect to the earlier described embodiments, cyclic energization of the electrically conductive coils 94, 96 with an electrical current generates a cyclically alternating magnetic field which interacts with the magnetic field of the oscillating member 98 to cause the oscillating member to oscillate between the extreme positions and, by so doing, alerts a patient in whom the medical device 78 is implanted. While the pole pieces 106, 108 may actually strike the peripheral flange 84 as described with respect to the earlier embodiments, in the construction illustrated in FIG. 8 the pole piece 106 impacts against and matingly engages the sidewall 90 when the oscillating member 98 reaches the first extreme position and the pole piece 108 impacts against and matingly engages the sidewall 92 when the oscillating member reaches the second extreme position.

Figure 9:
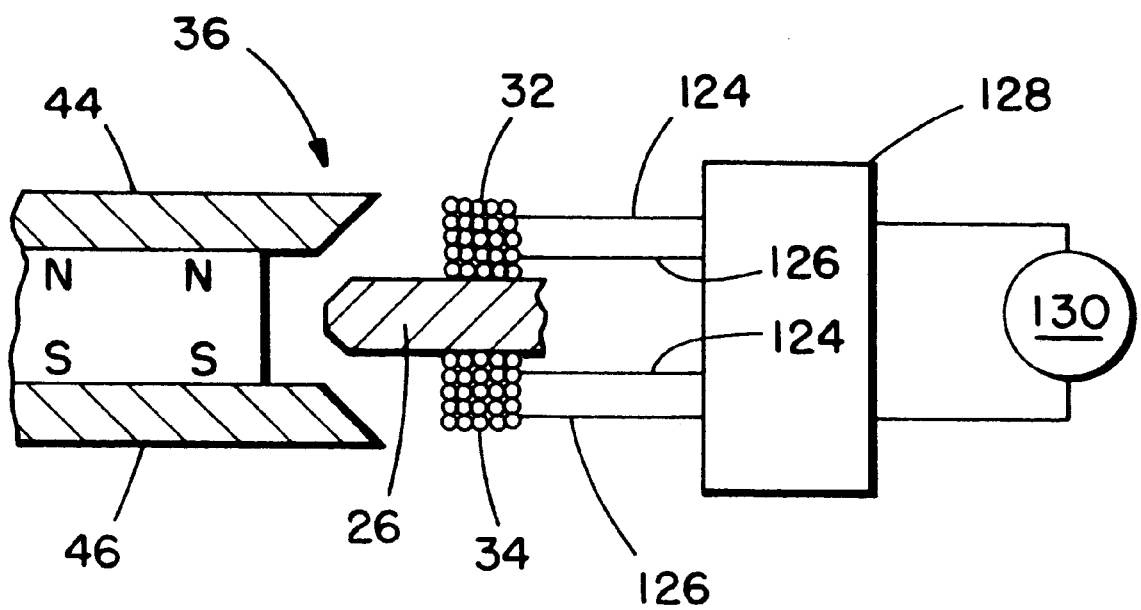
FIG. 9 is a schematic diagram of a motion sensor for monitoring the movement of a patient and constructed in the manner of the annunciator illustrated in the preceding views.

A structure very much similar to those already described can be used for detecting movement of a patient. Thus, as seen diagrammatically in FIG. 9, an activity sensor 120 may be encapsulated within a casing (not shown in this instance) and implantable in the body of a patient. The activity sensor 120 may have the construction of the annunciator 20 in FIG. 1, or in any of the other figures, as appropriate. However, for simplicity, the only components of that device illustrated in FIG. 12 are the electrically conductive coils 32, 34 and the oscillating member 36. It will be appreciated that in actual fact, all of the components illustrated in FIG. 1 are intended to be present in FIG. 9. In short, the movable mass of the oscillating member 36 will be affected by the motion, acceleration, or vibration of the patient and will generate a voltage across opposed leads 124, 126 from each of the conductive coils 32, 34, respectively, and a resulting current which is received and appropriately translated by a suitable output device 128 such as an amplifier, digital to analog converter, or comparator, then to a suitable circuit 130 intended to modify pacing parameters.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An annunciator for a medical device encapsulated within a casing and implantable in the body of a patient comprising:

a magnetically permeable stationary ring member including an integral inwardly projecting peripheral flange having first and second opposed sides;

a first electrically conductive coil mounted on the peripheral flange adjacent the first side;

a second electrically conductive coil mounted on the peripheral flange adjacent the second side;

an oscillating member encompassed by the stationary ring member including a planar magnet member having first and second opposed surfaces of opposite polarity and first and second planar pole pieces mounted to the first and second surfaces, respectively, in a sandwich-like construction, the oscillating member having a longitudinal axis and being movable along the axis between a first extreme position whereat the first pole piece is proximate the peripheral flange and a second extreme position whereat the second pole piece is proximate the peripheral flange; and axially compliant spider means extending between the oscillating member at the longitudinal axis and the ring member for biasing the oscillating member toward a neutral position intermediate the first and second extreme positions;

whereby cyclic energization of the first and second electrically conductive coils with an electrical current generates a cyclically alternating magnetic field which interacts with the magnetic field of the oscillating member to cause the oscillating member to oscillate between the first and second extreme positions.

2. An annunciator for a medical device, as set forth in claim 1:

wherein the first pole piece includes an outermost region terminating at a first beveled surface;

wherein the second pole piece includes an outermost region terminating at a second beveled surface;

wherein the peripheral flange includes an innermost region terminating at first and second beveled surfaces;

whereby the first beveled surface of the first pole piece impacts against and matingly engages the first beveled surface of the peripheral flange when the oscillating member reaches the first extreme position; and whereby the second beveled surface of the second pole piece impacts against and matingly engages the second beveled surface of the peripheral flange when the oscillating member reaches the second extreme position.

3. An annunciator for a medical device, as set forth in claim 1:

wherein the casing has a pair of opposed walls; and wherein the ring member is integral with at least one of the opposed walls of the casing of the medical device; and wherein the axially compliant spider means is substantially non-compliant transversely of the longitudinal axis for centering the oscillating member transversely relative to the ring member throughout travel thereof between the first and second extreme positions.

4. An annunciator for a medical device, as set forth in claim 1:

wherein the casing has a pair of opposed walls; and wherein the ring member is integral with and extends between the opposed walls of the casing of the medical device; and including:

first spider means having a central portion fixed to the first polar piece and a plurality of radially extending legs with terminal ends fixed, respectively, to the ring member at peripherally spaced locations, the first spider means being axially compliant and biasing the oscillating member toward a neutral position intermediate the first and second extreme positions, the first spider means being substantially non-compliant transversely of the longitudinal axis for centering the oscillating member relative to the ring member throughout travel thereof between the first and second extreme positions; and second spider means, co-operable with the first spider means, having a central portion fixed to the second polar piece and a plurality of radially extending legs with terminal ends fixed, respectively, to the ring member at peripherally spaced locations, the second spider means being axially compliant and biasing the oscillating member toward the neutral position, the second spider means being substantially non-compliant transversely of the longitudinal axis for centering the oscillating member relative to the ring member throughout travel thereof between the first and second extreme positions.

5. In combination with a medical device encapsulated within a casing and implantable in the body of a patient, an annunciator comprising:

a magnetically permeable stationary ring member fixed to the casing including an integral radially inwardly projecting peripheral flange having first and second opposed sides;

a first electrically conductive coil mounted on the peripheral flange adjacent the first side;

a second electrically conductive coil mounted on the peripheral flange adjacent the second side;

an oscillating member encompassed by the stationary ring member including a planar magnet member having first and second opposed surfaces of opposite polarity and first and second planar pole pieces mounted to the first and second surfaces, respectively, in a sandwich-like construction, the oscillating member having a longitudinal axis and being movable along the axis between a first extreme position whereat the first pole piece is proximate the peripheral flange and a second extreme position whereat the second pole piece is proximate the peripheral flange; and axially compliant spider means extending between the oscillating member at the longitudinal axis and the ring member for biasing the oscillating member toward a neutral position intermediate the first and second extreme positions;

whereby cyclic energization of the first and second electrically conductive coils with an electrical current generates a cyclically alternating magnetic field which interacts with the magnetic field of the oscillating member to cause the oscillating member to oscillate between the first and second extreme positions.

6. The combination of a medical device and an annunciator, as set forth in claim 5:

wherein the first pole piece includes an outermost region terminating at a first beveled surface;

wherein the second pole piece includes an outermost region terminating at a second beveled surface;

wherein the peripheral flange includes an innermost region terminating at a first and second beveled surfaces;

whereby the first beveled surface of the first pole piece impacts against and matingly engages the first beveled surface of the peripheral flange when the oscillating member reaches the first extreme position; and whereby the second beveled surface of the second pole piece impacts against and matingly engages the second beveled surface of the peripheral flange when the oscillating member reaches the second extreme position.

7. The combination of a medical device and an annunciator, as set forth in claim 5:

wherein the casing of the medical device includes opposed walls; and wherein the ring member is integral with and extends between the opposed walls of the casing of the medical device; and wherein the axially compliant spider means is substantially non-compliant transversely of the longitudinal axis for centering the oscillating member transversely relative to the ring member throughout travel thereof between the first and second extreme positions.

8. The combination of a medical device and an annunciator, as set forth in claim 5:

wherein the casing of the medical device includes opposed walls; and wherein the annunciator includes:

the ring member being integral with and extending between the opposed walls of the casing of the medical device, the peripheral flange being integral therewith and projecting transversely inwardly therefrom intermediate the opposed walls of the casing;

first spider means having a central portion fixed to the first polar piece and a plurality of radially extending legs with terminal ends fixed, respectively, to the ring member at peripherally spaced locations, the first spider means being axially compliant and biasing the oscillating member toward a neutral position intermediate the first and second extreme positions, the first spider means being substantially non-compliant transversely of the longitudinal axis for centering the oscillating member relative to the ring member throughout travel thereof between the first and second extreme positions; and second spider means, co-operable with the first spider means, having a central portion fixed to the second polar piece and a plurality of radially extending legs with terminal ends fixed, respectively, to the ring member at peripherally spaced locations, the second spider means being axially compliant and biasing the oscillating member toward the neutral position, the second spider means being substantially non-compliant transversely of the longitudinal axis for centering the oscillating member relative to the ring member throughout travel thereof between the first and second extreme positions.

9. The combination of a medical device and an annunciator, as set forth in claim 5:

wherein the casing of the medical device includes first and second opposed walls, respectively; and wherein the first pole piece impacts against and matingly engages the first opposed wall when the oscillating member reaches the first extreme position; and wherein the second pole piece impacts against and matingly engages the second opposed wall when the oscillating member reaches the second extreme position.

10. An activity sensor for a medical device encapsulated within a casing and implantable in the body of a patient comprising:

a magnetically permeable stationary ring member including an integral inwardly projecting peripheral flange having first and second opposed sides;

a first electrically conductive coil mounted on the peripheral flange adjacent the first side;

a second electrically conductive coil mounted on the peripheral flange adjacent the second side;

an oscillating member encompassed by the stationary ring member including a planar magnet member having first and second opposed surfaces of opposite polarity and first and second planar pole pieces mounted to the first and second surfaces, respectively, in a sandwich-like construction, the oscillating member having a longitudinal axis and being movable along the axis between a first extreme position whereat the first pole piece is proximate the peripheral flange and a second extreme position whereat the second pole piece is proximate the peripheral flange;

whereby relative motion between the oscillating member and the conductive coils imparted by movement of the casing causes interaction of the coil with the magnetic field of the oscillating member to produce a voltage and a resulting current through the coil which is proportional to velocity, thereby detecting activity on the part of the patient.

11. An annunciator for a medical device encapsulated within a casing and implantable in the body of a patient comprising:

a magnetically permeable stationary ring member including an integral inwardly projecting peripheral flange having first and second opposed sides;

a first electrically conductive coil mounted on the peripheral flange adjacent the first side;

a second electrically conductive coil mounted on the peripheral flange adjacent the second side;

a free floating oscillating member encompassed by the stationary ring member including a planar magnet member having first and second opposed surfaces of opposite polarity and first and second planar pole pieces mounted to the first and second surfaces, respectively, in a sandwich-like construction, the oscillating member having a longitudinal axis and being movable along the axis between a first extreme position whereat the first pole piece is proximate the peripheral flange and a second extreme position whereat the second pole piece is proximate the peripheral flange;

whereby cyclic energization of the first and second electrically conductive coils with an electrical current generates a cyclically alternating magnetic field which interacts with the magnetic field of the oscillating member to cause the oscillating member to oscillate between the first and second extreme positions.

12. An annunciator for a medical device, as set forth in claim 11:

wherein the first pole piece includes an outermost region terminating at a first beveled surface;

wherein the second pole piece includes an outermost region terminating at a second beveled surface;

wherein the peripheral flange includes an innermost region terminating at first and second beveled surfaces;

whereby the first beveled surface of the first pole piece impacts against and matingly engages the first beveled surface of the peripheral flange when the oscillating member reaches the first extreme position; and whereby the second beveled surface of the second pole piece impacts against and matingly engages the second beveled surface of the peripheral flange when the oscillating member reaches the second extreme position.

13. In combination with a medical device encapsulated within a casing and implantable in the body of a patient, an annunciator comprising:

a magnetically permeable stationary ring member fixed to the casing including an integral radially inwardly projecting peripheral flange having first and second opposed sides;

a first electrically conductive coil mounted on the peripheral flange adjacent the first side;

a second electrically conductive coil mounted on the peripheral flange adjacent the second side;

a free floating oscillating member encompassed by the stationary ring member including a planar magnet member having first and second opposed surfaces of opposite polarity and first and second planar pole pieces mounted to the first and second surfaces, respectively, in a sandwich-like construction, the oscillating member having a longitudinal axis and being movable along the axis between a first extreme position whereat the first pole piece is proximate the peripheral flange and a second extreme position whereat the second pole piece is proximate the peripheral flange;

whereby cyclic energization of the first and second electrically conductive coils with an electrical current generates a cyclically alternating magnetic field which interacts with the magnetic field of the oscillating member to cause the oscillating member to oscillate between the first and second extreme positions.

14. The combination of a medical device and an annunciator, as set forth in claim 13:

wherein the first pole piece includes an outermost region terminating at a first beveled surface;

wherein the second pole piece includes an outermost region terminating at a second beveled surface;

wherein the peripheral flange includes an innermost region terminating at a first and second beveled surfaces;

whereby the first beveled surface of the first pole piece impacts against and matingly engages the first beveled surface of the peripheral flange when the oscillating member reaches the first extreme position; and whereby the second beveled surface of the second pole piece impacts against and matingly engages the second beveled surface of the peripheral flange when the oscillating member reaches the second extreme position.

15. The combination of a medical device and an annunciator, as set forth in claim 13:

wherein the casing of the medical device includes first and second opposed walls, respectively; and wherein the first pole piece impacts against and matingly engages the first opposed wall when the oscillating member reaches the first extreme position; and wherein the second pole piece impacts against and matingly engages the second opposed wall when the oscillating member reaches the second extreme position.

* * * * *